(12) United States Patent
Chong et al.

(10) Patent No.: US 11,366,191 B2
(45) Date of Patent: Jun. 21, 2022

(54) DYNAMIC BIONIC HEART PHANTOM USED FOR MAGNETIC RESONANCE IMAGING SYSTEM, CONTROL METHOD AND TESTING METHOD THEREOF

(71) Applicant: THE SECOND AFFILIATED HOSPITAL OF PLA ARMY MEDICAL UNIVERSITY, Chongqing (CN)

(72) Inventors: YinBao Chong, Chongqing (CN); Peng Zhao, Chongqing (CN); WenCai Pan, Chongqing (CN); Lang Lang, Chongqing (CN); Jingjing Xiao, Chongqing (CN); Jieshi Ma, Chongqing (CN); Meng Li, Chongqing (CN); ShiHui Zhang, Chongqing (CN)

(73) Assignee: THE SECOND AFFILIATED HOSPITAL OF PLA ARMY MEDICAL UNIVERSITY, Chongqing (CN)

(*) Notice: Subject to any disclaimer, the term of this patent is extended or adjusted under 35 U.S.C. 154(b) by 241 days.

(21) Appl. No.: 16/754,374

(22) PCT Filed: Feb. 13, 2019

(86) PCT No.: PCT/CN2019/074922
§ 371 (c)(1),
(2) Date: Apr. 8, 2020

(87) PCT Pub. No.: WO2020/124761
PCT Pub. Date: Jun. 25, 2020

(65) Prior Publication Data
US 2021/0215784 A1    Jul. 15, 2021

(30) Foreign Application Priority Data
Dec. 17, 2018  (CN) .......................... 201811544324.6

(51) Int. Cl.
*G01R 33/58* (2006.01)
*A61B 5/318* (2021.01)
(Continued)

(52) U.S. Cl.
CPC ............ *G01R 33/58* (2013.01); *A61B 5/0006* (2013.01); *A61B 5/055* (2013.01); *A61B 5/318* (2021.01);
(Continued)

(58) Field of Classification Search
USPC ....................................................... 324/307
See application file for complete search history.

(56) References Cited

U.S. PATENT DOCUMENTS 10,271,794 B2 * 4/2019 Olson .................... A61B 5/287
10,821,306 B2 * 11/2020 Yue ....................... A61N 5/1075
(Continued)

FOREIGN PATENT DOCUMENTS

CN         1846605      10/2006
CN       101618239       1/2010
(Continued)

OTHER PUBLICATIONS

"International Search Report (Form PCT/ISA/210) of PCT/CN2019/074922," dated Jun. 4, 2019, pp. 1-4.
(Continued)

*Primary Examiner* — Rodney E Fuller
(74) *Attorney, Agent, or Firm* — JCIP Global Inc.

(57) ABSTRACT

A dynamic bionic heart phantom is used for an MRI system, a control method and a testing method. The dynamic bionic heart phantom includes a bionic heart phantom, a control system, positive pressure devices and a negative pressure device; the bionic heart phantom includes a water tank and a heart phantom arranged in the water tank, and the heart phantom is connected to the control system through four air
(Continued)

pipes; the control system includes an antimagnetic control device and a control PC, and the antimagnetic control device is composed of a measurement and control module, four proportional flow values, a power module and a magnetic shielding box; the positive pressure devices, including gas, gas cylinders and pressure reducing valves, are connected to two gas inlet interfaces of the control system respectively; and the negative pressure device includes a vacuum pump and a negative pressure container.

8 Claims, 7 Drawing Sheets

(51) Int. Cl.
    *A61B 5/00*          (2006.01)
    *A61B 5/055*        (2006.01)
    *G01R 33/54*        (2006.01)

(52) U.S. Cl.
    CPC .......... *A61B 5/7221* (2013.01); *A61B 5/7292* (2013.01); *G01R 33/543* (2013.01)

(56) References Cited

U.S. PATENT DOCUMENTS

| | | | |
|---|---|---|---|
| 11,176,849 B2* | 11/2021 | Fatimi | G16H 50/50 |
| 2010/0167251 A1* | 7/2010 | Boutchko | A61B 6/5247 |
| | | | 434/267 |
| 2013/0196301 A1* | 8/2013 | Carson | G09B 23/288 |
| | | | 434/268 |
| 2014/0069215 A1* | 3/2014 | Tavakoli | A61B 8/587 |
| | | | 264/299 |
| 2016/0027345 A1* | 1/2016 | Carson | G09B 23/32 |
| | | | 434/262 |
| 2017/0224279 A1 | 8/2017 | Gahan et al. | |
| 2020/0160753 A1* | 5/2020 | Sadasivan | G16H 50/50 |
| 2021/0043113 A1* | 2/2021 | Sadasivan | G09B 23/285 |
| 2021/0212654 A1* | 7/2021 | Zhao | A61B 6/465 |

FOREIGN PATENT DOCUMENTS

| | | |
|---|---|---|
| CN | 102930771 | 2/2013 |
| CN | 103330963 | 10/2013 |
| CN | 106237409 | 12/2016 |
| JP | 2010125087 | 6/2010 |

OTHER PUBLICATIONS

Zhao Peng, et al., "Application of dynamic heart phantom for quality control of cardiac computed tomography imaging," Chinese Journal of Medical Physics, vol. 35, Jun. 2018, pp. 659-665.

Nolan E. Swailes, et al., "Dynamic Phantom with Heart, Lung, and Blood Motion for Initial Validation of MRI Techniques," Journal of Magnetic Resonance Imaging, vol. 34, Dec. 2011, pp. 941-946.

* cited by examiner

DYNAMIC BIONIC HEART PHANTOM USED FOR MAGNETIC RESONANCE IMAGING SYSTEM, CONTROL METHOD AND TESTING METHOD THEREOF

CROSS-REFERENCE TO RELATED APPLICATION

This application is a 371 of international application of PCT application serial no. PCT/CN2019/074922, filed on Feb. 13, 2019, which claims the priority benefit of China application no. 201811544324.6, filed on Dec. 17, 2018. The entirety of each of the above mentioned patent applications is hereby incorporated by reference herein and made a part of this specification.

TECHNICAL FIELD

The invention belongs to the technical field of quality control standardization of digital diagnosis and treatment equipment, and particularly relates to a dynamic bionic heart phantom used for magnetic resonance imaging (MRI) system, a control method and a testing method.

BACKGROUND OF THE INVENTION

A medical MRI device, one of the advanced medical imaging diagnostic devices, is more advantageous in examination of brain, heart, lung, abdomen, blood vessels and joints, especially in clinical application of advanced imaging techniques such as functional magnetic resonance imaging (fMRI), MR (Magnetic Resonance) cardiac function imaging, MR angiography imaging (MRA), and MR spectral imaging (MRSI). However, in recent years, with the rapid application of automatic intelligent assisted diagnosis and treatment functions of MRI clinical application software, on the one hand, the quality control range of traditional medical equipment is gradually subverted due to that the price of related software has approached 50% of the price of the entire MRI device; and on the other hand, cases of potential safety hazards, medical malpractices, and injury to patients or operators are also common due to insufficient understanding of its potential risks and quality of clinical application. How to control the quality of the MRI clinical application software, reduce clinical application risks and improve hospital medical quality, comprehensive benefits and safety, has been concerned by MRI device manufacturers and medical and health institutions gradually and widely.

The quality control of the MRI device finally aims at minimizing risks and costs while high-quality images that fully meet diagnostic requirements are acquired. Currently, related standards and performance testing phantoms established for quality control of the MRI device by the American Association of Physicists in Medicine (AAPM) and the American College of Radiology (ACR), including Magphan ANDI, an SMR100/170 phantom and an ACR phantom of American Phantom Laboratory, the two static phantoms of which, can realize testing and evaluation of physical performance indexes of hardware of the MRI device such as signal-to-noise ratio (SNR), image uniformity, spatial linearity, spatial resolution, layer thickness, aspect ratio and magnetic field uniformity. However, quality control of clinical application software with an advanced MRI function is still at the theoretical research and experimental testing stage at home and abroad, and is especially short of phantoms for quality control and safety evaluation of clinical application software about cardiac functions imaging and vascular diseases imaging in the aspects such as organ motion and blood flow.

Therefore, it is necessary to develop a new dynamic bionic heart phantom used for the MRI system, a control method and a testing method.

SUMMARY OF THE INVENTION

An object of the present invention is to provide a dynamic bionic heart phantom used for an MRI system and a control method thereof. The dynamic bionic heart phantom can be used for simulating the anatomical structure and motion characteristics of a human heart, has standard models of a normal heart and hearts with typical cardiac diseases, outputs ECG signals simultaneously and can be applied to testing and evaluation of imaging quality of the MRI system.

The dynamic bionic heart phantom for the MRI system comprises a bionic heart phantom, a control system, a negative pressure device and positive pressure devices;

The bionic heart phantom comprises a water tank, and a heart phantom arranged in the water tank; the heart phantom has four chambers, respectively including, a left atrium chamber, a right atrium chamber, a left ventricular chamber and a right ventricular chamber, wherein the left atrium chamber is connected to the left ventricular chamber through a one-way valve, and the right atrium chamber is connected to the right ventricular chamber through a one-way valve;

The control system comprises an antimagnetic control device and a control PC; the antimagnetic control device includes a magnetic shielding box, a measurement and control module, four proportional flow valves, a power module, an Ai1 interface, an Ai2 interface, a Vo1 interface, a Vo2 interface, an Ai1' interface, an Ai2' interface, a Vo1' interface, a Vo2' interface, a J1 interface, a J2 interface and an ECG interface. The measurement and control module, the four proportional flow valves and the power module are arranged in the magnetic shielding box: and the Ai1 interface, the Ai2 interface, the Vo1 interface, the Vo2 interface, the Ai1' interface, the Ai2' interface, the Vo1' interface, the Vo2' interface, the J1 interface, the J2 interface and the ECG interface are arranged on the magnetic shielding box 15.

The measurement and control module comprises a multi-channel I/O interface, a micro processing system and an ECG output module; and the micro processing system is connected with the four proportional flow valves, the ECG output module and the negative pressure device through the multi-channel I/O interface respectively to transmit corresponding control signals to the four proportional flow valves and the vacuum pump, transmit ECG analog signals to the ECG output module synchronously, and collect feedback signals of the four proportional flow valves in real time;

The four proportional flow valves includes a proportional flow valve Ai1, a proportional flow valve Ai2, a proportional flow valve Vo1, and a proportional flow valve Vo2; the gas outlet end of the proportional flow valve Ai1 is connected with the right atrium chamber of the heart phantom through the Ai1 interface and the air pipe; the gas inlet end of the proportional flow valve Ai1 is connected to one of the positive pressure devices through the Ai1' interface and the air pipe; the gas outlet end of the proportional flow valve Ai2 is connected to the left atrium chamber of the heart phantom through the Ai2 interface and the air pipe; the gas inlet of the proportional flow valve Ai2 is connected to the other positive pressure device through the Ai2' interface and the air pipe; the gas outlet end of the proportional flow valve Vo1 is connected to the right ventricular chamber of the heart phantom through the Vo1 interface and the air pipe; the gas inlet end of the proportional flow valve Vo1 is connected to the negative pressure device through the Vo1' interface and the air pipe; the gas outlet end of the proportional flow valve Vo2 is connected to the left ventricular chamber of the heart phantom through the Vo2 interface and the air pipe; the gas inlet end of the proportional flow valve Vo2 is connected to the negative pressure device through the Vo2' interface and the air pipe; and the four proportional flow valves are also connected to the measurement and control module separately to receive control signals and transmit feedback signals.

The power module is connected to the measurement and control module and the four proportional flow valves respectively to provide working power to the measurement and control module and the four proportional flow valves.

Furthermore, the ECG output module comprises a high precision operational amplifier differential circuit, a resistance network circuit, an LA electrode interface, an RA electrode interface, and an LL electrode interface and an RL electrode interface; the resistance network circuit is connected to the high precision operational amplifier differential circuit and is also connected to the LA electrode interface, the RA electrode interface, the LL electrode interface, and the RL electrode interface, respectively to convert the ECG analog signals transmitted by the micro processing system to ECG signals for simulating limb leads; the LA electrode interface, the RA electrode interface, the LL electrode interface, and the RL electrode interface are connected to the MRI device via an ECG lead wire through an ECG interface of the antimagnetic control device.

Furthermore, the magnetic shielding box comprises a box, a top cover, a handle and connectors all of which are made of an aluminum plate; and ten extension tubes with waveguide holes, respectively used for installation of eight air pipes, one shielding wire, one USB cable with the shielding wire and the ECG lead wire, are arranged on both sides of the box.

Furthermore, two groups of the positive pressure devices are provided, each of which comprises a gas cylinder and a pressure reducing valve; the gas cylinder, filled with gas, is connected with a pressure reducing valve; the gas inlet end of the proportional flow valve Ai1 is connected to one positive pressure device having a pressure output value of 0.5 MPa at the Ai1 interface through the Ai1' interface and the air pipe; and the gas inlet end of the proportional flow valve Ai2 is connected to the other positive pressure device with the pressure output value of 1.5 MPa at the Ai2 interface through the Ai2' interface and the air pipe.

Furthermore, said vacuum device comprises a vacuum pump and a vacuum container; the vacuum pump is connected to the antimagnetic control device through a lead wire to receive control signals and is also connected to the negative pressure container through the air pipe; and the negative pressure container is connected to the Vo1' interface and the Vo2' interfaces of the antimagnetic control device through the air pipes to recover gases.

Furthermore, the multi-channel I/O interface is connected to the analog input interfaces of the four proportional flow valves respectively through four analog output interfaces, and the analog input interfaces of the proportional flow valves are used for receiving control pulse signals.

The multi-channel I/O interface is connected to the analog output interfaces of the four proportional flow valves respectively through eight analog input interfaces, and said analog output interfaces of the four proportional flow valves are used for feeding back gas pressure or flow data.

The multi-channel I/O interface is connected to the ECG output module through an analog output interface to output ECG analog signals.

The multi-channel IO interface is connected to the vacuum pump via the J2 interface of the antimagnetic control device and the shielding wire through one analog output interface to output control driving signals.

The multi-channel I/O interface is connected to the control PC via a J1 interface of the antimagnetic control device through the USB cable with the shielding wire.

A control method of the dynamic bionic heart phantom, adopting the dynamic bionic heart phantom used for MRI system of the invention, comprises the following steps.

The control PC transmits corresponding pulse signals to the four proportional flow valves respectively through the multi-channel I/O interface, and each proportional flow valve is opened or closed correspondingly based on the pulse signal corresponding to itself and feeds back gas pressure or flow data to the control PC in real time, and the control PC adjusts the pulse signals based on the fed-back gas pressure or flow data, that is, simulates the motion of heart chambers at different heart rate cycles; the control PC while transmitting the pulse signals generates the ECG signals at the same time and transmits the signals to the MRI device through the ECG output module and the ECG lead wire to trigger ECG gating during heart scanning of MRI device.

A testing method of the imaging quality of the MRI system, using the dynamic bionic heart phantom used for the MRI system of the disclosure, comprises the following steps.

First, placing the control PC, the positive pressure devices and the negative pressure device in an MRI control room; putting the bionic heart phantom and the antimagnetic control device on a scanning bed in an MRI scanning room; placing the bionic heart phantom in an RF coil and adjusting the bed to be in an MRI scan range; and ensuring that the antimagnetic control device is located 1 m outside the edge of the main magnet of the MRI device.

Next, opening the positive pressure devices respectively; setting control parameters in the control PC, starting running the system after the equilibrium state thereof is built and, by the control PC, transmitting a control command to the microprocessing system in real time; transmitting corresponding pulse signals to the four proportional flow valves through the multi-channel I/O interface to enable the proportional flow valves to be open or closed based on the received corresponding pulse signals; feeding back gas pressure or flow data to the control PC in real time by the proportional flow valves; by the control PC, adjusting the pulse signals based on the fed-back gas pressure or flow data, that is, simulating the motion of the heart chambers at different heart rate cycles; generating the ECG signals while the control PC transmits the pulse signals, and transmitting the signals to the MRI device through the ECG output module and the ECG lead wire to trigger ECG gating during heart scanning of the MRI device; and Finally, performing post-processing and 3D reconstruction by utilizing clinical application software of the MRI device to obtain relevant evaluation indexes of the bionic heart phantom, and performing evaluation on functional conformity of the MRI device.

The present invention has the following advantages.

(1) The anatomical structure and motion characteristics of a human heart can be simulated.

(2) Both the normal heart and the hearts with typical heart diseases can be simulated, with the synchronous output of ECG signals.

(3) The dynamic bionic heart phantom can satisfy the needs of conformity evaluation researches on the MRI device and the clinical application software thereof.

(4) The imaging quality of the MRI device can be demonstrated accurately and truly.

(5) The dynamic bionic heart phantom is applicable to MRI devices of less than or equal to 1.5T.

DETAILED DESCRIPTION OF THE INVENTION

The invention will be further described below with reference to the accompanying drawings.

Figure 1:
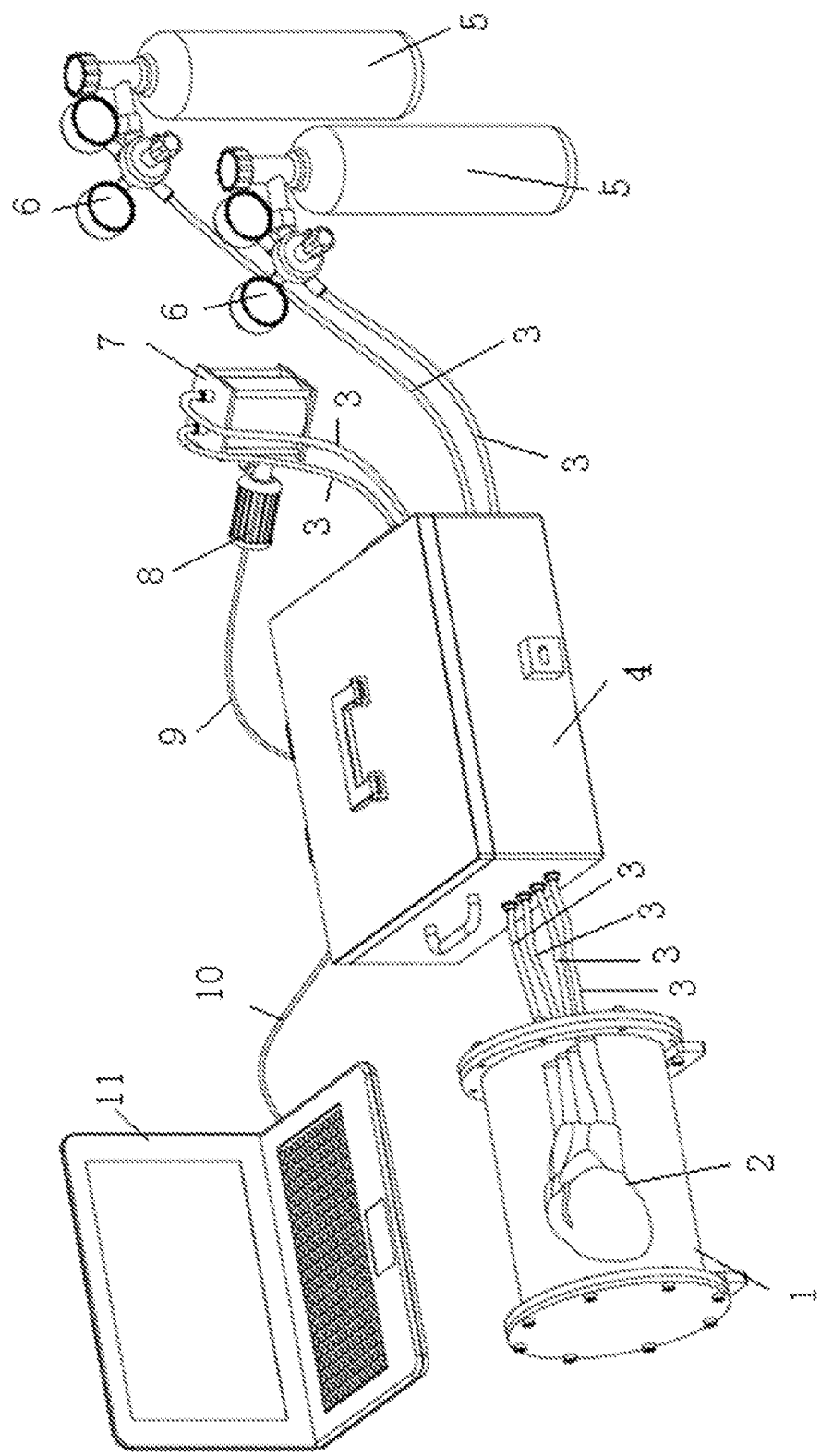
FIG. 1 is a schematic view of the structure of the invention.

I. Phantom Structure:

As shown in FIG. 1, the dynamic bionic heart phantom used for the MRI system in the embodiment comprises a bionic heart phantom, a control system, positive pressure devices 16 and a negative pressure device.

Bionic Heart Phantom:

As shown in FIG. 1, the bionic heart phantom in the embodiment comprises a water tank 1 and a heart phantom 2.

In this embodiment, the water tank 1 is a cylindrical organic glass container, which is 343 mm long, 256 mm wide and 259 mm high and filled with water, is used for installation and fixation of the heart phantom 2. Both sides of the water tank 1 are fixed by flanges, rubber rings and aluminum countersunk screws, and centers of the flanges on one side are provided with holes for installation of a central disc; the central disc has four via holes with apertures reduced progressively; the four via holes are arranged in parallel for installation and fixation of the four air pipes 3 in connection with the heart phantom 2, and are further sealed by rubber rings; and the upper side of the water tank 1 is provided with an opening.

Figure 3:
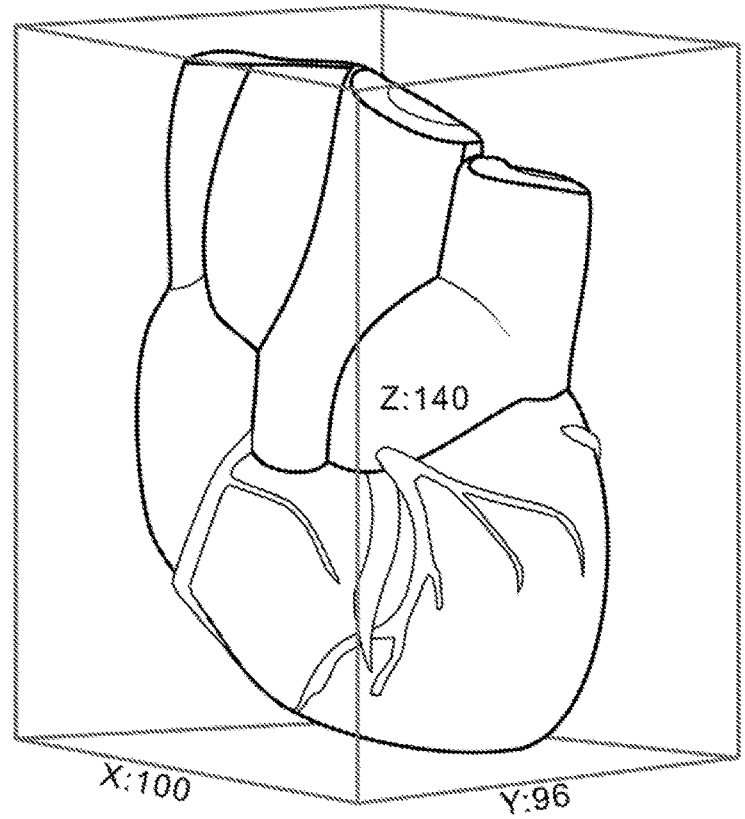
FIG. 3 is a schematic structural view of a bionic heart phantom in the invention.

As shown in FIG. 3, the heart phantom 2 in the embodiment, being 100 mm long, 96 mm wide and 140 mm high, comprises four chambers, respectively including, a left atrium chamber, a right atrium chamber, a left ventricular chamber, and a right ventricular chamber, wherein the left atrium chamber is connected to the left ventricular chamber through a one-way valve (i.e., when the one-way valve is open, gas in the left atrium chamber enters the left ventricular chamber), and the right atrium chamber is connected to the right ventricular chamber through a one-way valve (i.e., when the check valve is open, gas in the right atrium chamber can enter the right ventricular chamber only); the heart phantom, used for simulating the four chambers, the septum, the pericardium and the blood vessels of an adult heart, has the same MR signal intensity (70-120 mean value) as a real heart; the four chambers are used for simulating the left atrium, the left ventricle, the right atrium and right ventricle respectively, the two one-way valves are used for simulating a mitral valve and a tricuspid valve respectively and the four air pipes 3 are connected to the Ai1 interface, the Ai2 interface, the Vo1 interface and the Vo2 interface of the antimagnetic control device 4 respectively, among them, two of the air pipes 3 connected to the Ai1 interface and the Ai2 interface communicate with the right atrium chamber and the left atrium chamber respectively and the other two air pipes connected to the Vo1 interface and the Vo2 interface communicate with the right ventricular chamber and the left ventricular chamber respectively.

Figure 2:
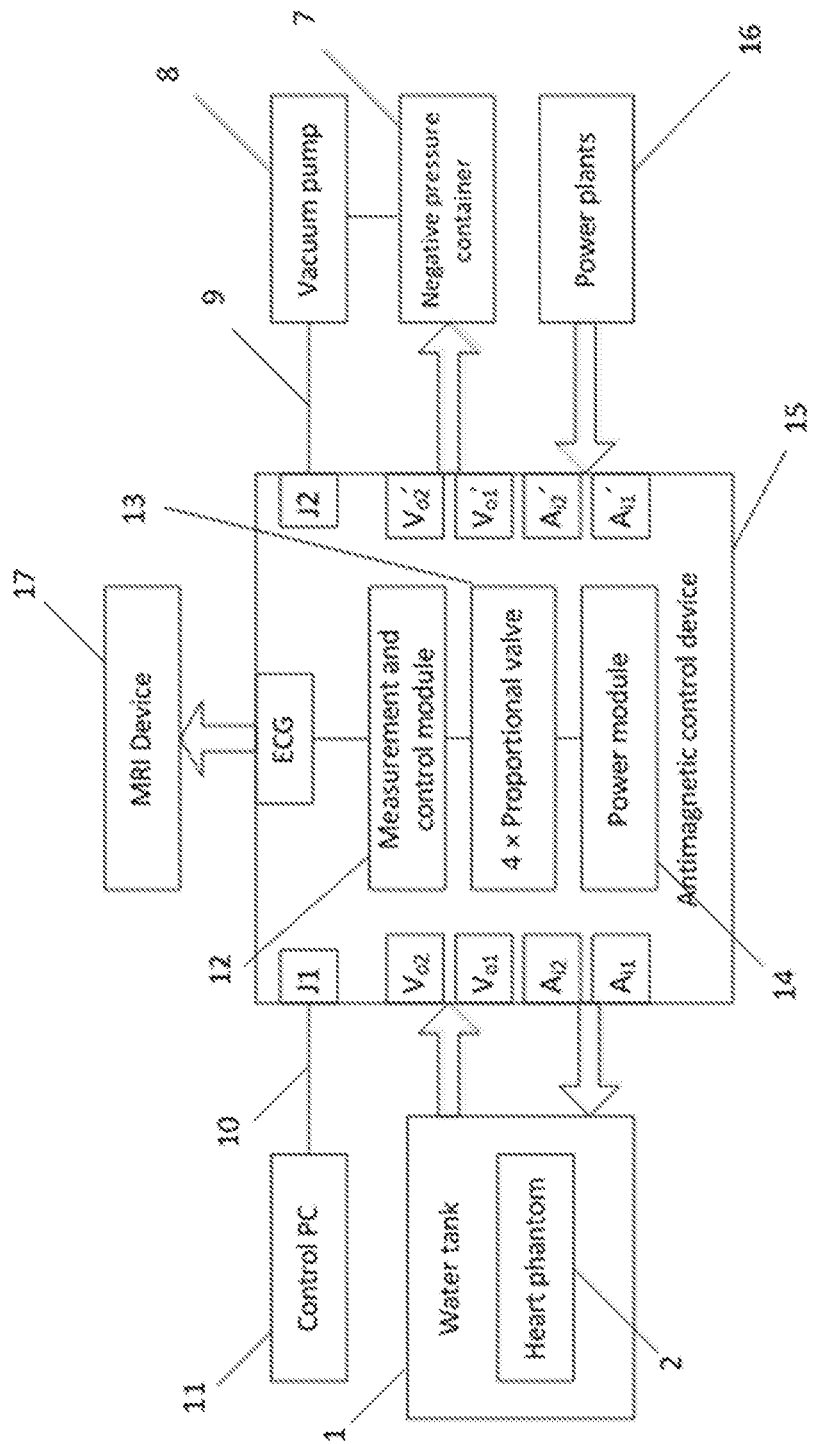
FIG. 2 is a schematic block diagram of the invention.

Control System:

As shown in FIG. 2, the control system in the embodiment comprises an antimagnetic control device 4 and a control PC 11; and the antimagnetic control device 4 comprises four proportional flow valves 13, a measurement and control module 12, a power module 14 and a magnetic shielding box 15.

In this embodiment, the proportional flow valve 13 (for example, the proportional flow valve 13 with the model of CP20X, made by Ambulance (Shenzhen) Technology Co., Ltd.) comprises a VCC interface serving as the positive pole of the working voltage DC 24V, an analog input interface for reception of the control pulse signals, an analog output interface for feedback of the gas pressure or flow data and a GND interface serving as the negative pole. The four proportional flow valves 13 are a proportional flow valve Ai1, a proportional flow valve Ai2, a proportional flow valve Vo1, and a proportional flow valve Vo2.

The gas outlet end of the proportional flow valve Ai1 is connected to the right atrium chamber of the heart phantom 2 through the Ai1 interface and the air pipe 3, and the gas inlet end thereof is connected to the positive pressure device 16 through the Ai1' interface and the air pipe 3.

The gas outlet end of the proportional flow valve Ai2 is connected to the left atrium chamber of the heart phantom 2, and the gas inlet end thereof is connected to the positive pressure device 16 through the Ai2' interface and the air pipe 3.

The gas outlet end of the proportional flow valve Vo1 is connected to the right ventricular chamber of the heart phantom 2 through the Vo1 interface and the air pipe 3, and the gas inlet end thereof is connected to the negative pressure device through the Vo1' interface and the air pipe 3.

The gas outlet end of the proportional flow valve Vo2 is connected to the left ventricular chamber of the heart phantom 2 through the Vo2 interface and the air pipe 3; and the gas inlet end thereof is connected to the negative pressure device through the Vo2' interface and the air pipe 3.

The four proportional flow valves 13 are connected to the measurement and control module 12 through eight lead wires to receive control signals and transmit feedback signals.

The measurement and control module 12 comprises a multi-channel I/O interface, a micro processing system and an ECG output module; a multifunctional I/O device made by NI is adopted for the micro processing system and the multi-channel I/O interface; the four analog output interfaces AO0 to AO3 are connected to the analog input interfaces of the four proportional flow valves respectively to transmit the control pulse signals; the four analog input interfaces AI0 to AI3 are connected to the analog output interfaces of the four proportional flow valves 13 respectively to receive the gas pressure or flow data; the analog output interface AO4 is connected to the ECG output module to output ECG analog signals; and the analog output interface AO5 is connected to the vacuum pump 8 to output the control driving signals and is also connected to the control PC 11 through the USB cable with the shielding wire 10.

Figure 6:
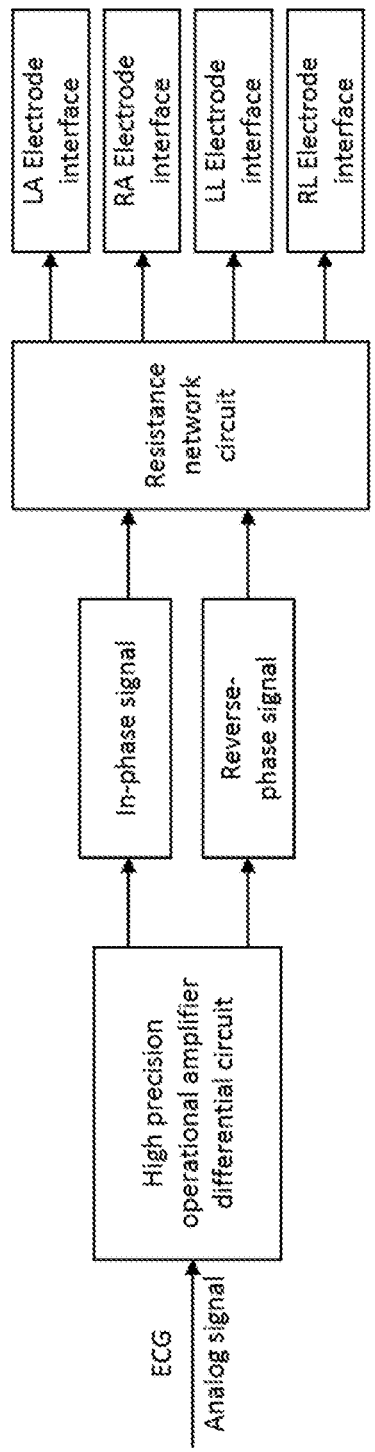
FIG. 6 is a block diagram of an ECG signal output circuit in the invention.

As shown in FIG. 6, the ECG output module in the embodiment is composed of a high precision operational amplifier differential circuit, a resistance network circuit, and an LA electrode interface (left arm drive electrode interface), an RA electrode interface (right arm electrode interface), and an LL electrode interface (left leg electrode interface) and an RL electrode interface (right leg electrode interface). The ECG output module is configured to convert the ECG analog signals transmitted by the micro processing system to ECG signals used for simulating limb leads. The ECG analog signals (level range from 0.5V to 9.5V) are converted to in-phase and reverse-phase signals by the high precision operational amplifier differential circuit, and the in-phase and reverse-phase signals are respectively subjected to voltage division by the resistance network circuit to obtain signals in a normal ECG range. (R wave peak value is not greater than 5 mV). The LA electrode interface, the RA electrode interface, the LL electrode interface, and the RL electrode interface are connected to different voltage dividing points respectively, thereby forming differential signals of the limb leads and outputting resistances in accordance with the output resistance characteristics of human ECG signals. The amplitude ratio of each limb lead is variable along with modification of the resistance of the resistance network circuit and is shown in Table 1:

Table 1 Amplitude ratio of each lead

| Name of lead | Ratio |
|---|---|
| I | 1 |
| II | 3/2 |
| III | 1/2 |
| aVL | 1/4 |
| aVR | −5/4 |
| aVF | 1 |

In this embodiment, the power module 14 comprises a rechargeable lithium battery pack, a power management circuit and a filter circuit, and may provide working power for the measurement and control module 12 and the proportional flow valve 13. The rechargeable lithium battery pack is composed of eight 25.9 V lithium battery packs (standard 18650 lithium batteries), seven of which are connected in series and rest one of which is connected in parallel. The power management circuit, responsible for battery charging and discharging, power supply output and switching-on/off, has the charging voltage of DC 12-24V, the charging time of less than 8 hours, the maximum discharge current of 10 A, and the three output voltages of DC 5V, 12V and 24V and provides power to the micro processing system, the multi-channel I/O interface, the proportional flow valve 13 and the ECG output module, respectively. The filter circuit is installed mainly on the power output interface and the switching-on/off button interface for magnetic filtering.

Figure 4:
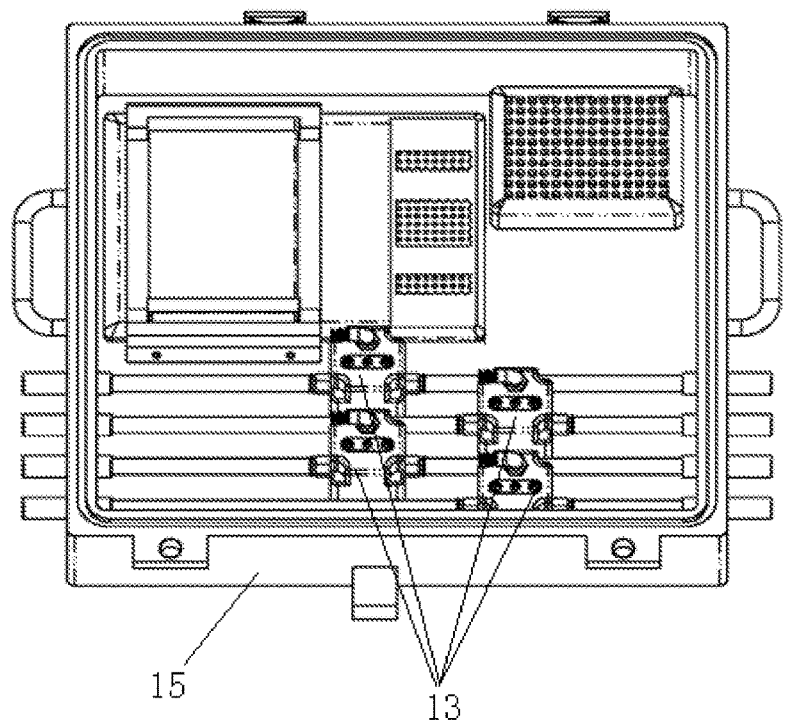
FIG. 4 is a schematic structural view of a magnetic shielding box in the invention.

As shown in FIG. 4, the magnetic shielding box 15 in the embodiment comprises a box made of a 20 mm aluminum plate, a top cover, a handle and connectors; ten extension tubes with waveguide holes, used for installation of eight air pipes 3, one lead wire, one USB cable with the shielding wire 10 and an ECG lead wire respectively, are arranged on both sides of the box; and as the waveguide holes are filtered and shielded, not only the measurement and control module 12, each proportional flow valve 13 and the power module 14 are guaranteed to work normally, but also disturbance to uniformity of the magnetic field which may affect normal operation of the MRI device 7 is prevented. The top cover, the handle and the connectors are made of aluminum materials and are compatible with all the MRI devices 17.

Control PC:

In this embodiment, host computer software, developed by using LabVIEW and the Lab Windows CVI programming platforms and using the NI-DAQmx capture card hardware driver as the carrier, is installed in the control PC 11 and is composed of a hardware drive engine, a data acquisition engine, a closed-loop control engine, a system state engine and a UI interface. Among them, the hardware drive engine optimizes the logic relationship of the NI DAQmx drive program and timing sequences of input and output signal, in combination with a multifunctional IO device, to meet functional requirements of other application interfaces; the data acquisition engine calculates phase length of each heart motion period according to a heart rate preset value and performs re-sampling and data packing and analysis on the acquired analog quantity and the output analog quantity; the closed-loop control engine compares the flow feedback value corresponding to one moment of the corresponding heart motion period based on a preset volume and time relationship of each chamber, calculates the control pulse time sequence of each proportional flow valve 13 based on an intelligent control algorithm (such as a PID controller) and synthesizes the analog ECG waveform synchronously; the system state engine obtains real-time data such as analog heart rate, volume, gas path flow and pressure, and monitors each state index of inner thread after the system runs; and the UI (User Interface) is a human-computer interaction interface which has five functional interfaces, including, a parameter setting interface, a system self-testing interface, an equilibrium establishment interface and a system analysis interface.

Positive Pressure Devices:

In the embodiment, two groups of the positive pressure devices 16 are provided, each of which comprises a gas cylinder 5 and a pressure reducing valve 6; the gas cylinder 5, filled with gas, is connected with a pressure reducing valve 6; the gas inlet end of the proportional flow valve Ai1 is connected to one o positive pressure device 16 having a pressure output value of 0.5 MPa at the Ai1 interface through the Ai1' interface and the air pipe 3; and the gas inlet end of the proportional flow valve Ai2 is connected to the other positive pressure device 16 with the pressure output value of 1.5 MPa at the Ai2 interface end through the Ai2' interface and the air pipe 3. In this embodiment, the gas is nitrogen (99.9%), and the gas cylinder 5 is a 9L glass fiber bottle.

Negative Pressure Device:

The negative pressure device comprises a vacuum pump 8 and a negative pressure container 7. In this embodiment, the negative pressure container 7, the top and the bottom of which are made of square aluminum alloy blocks and the periphery of which are reinforced by four parallel high-strength aluminum alloy strips, is a 20L cylindrical organic glass container; two one-way valves for connecting to the Vo1' interface and the Vo2' interface of the antimagnetic control device 4 through the air pipe 3 are arranged on the top of the negative pressure container 7, and an interface used for connecting to the vacuum pump 8 is arranged at the downside. The vacuum pump 8 is connected to the antimagnetic control device 4 through a shielding wire 9 and is also connected to the negative pressure container 7 through the gas pipe 3; and the negative pressure container 7 is connected to the Vo1' interface and the Vo2' interface of the antimagnetic control device 4 through the gas pipe 3 to recover gases.

II. Phantom Control Method

Figure 8:
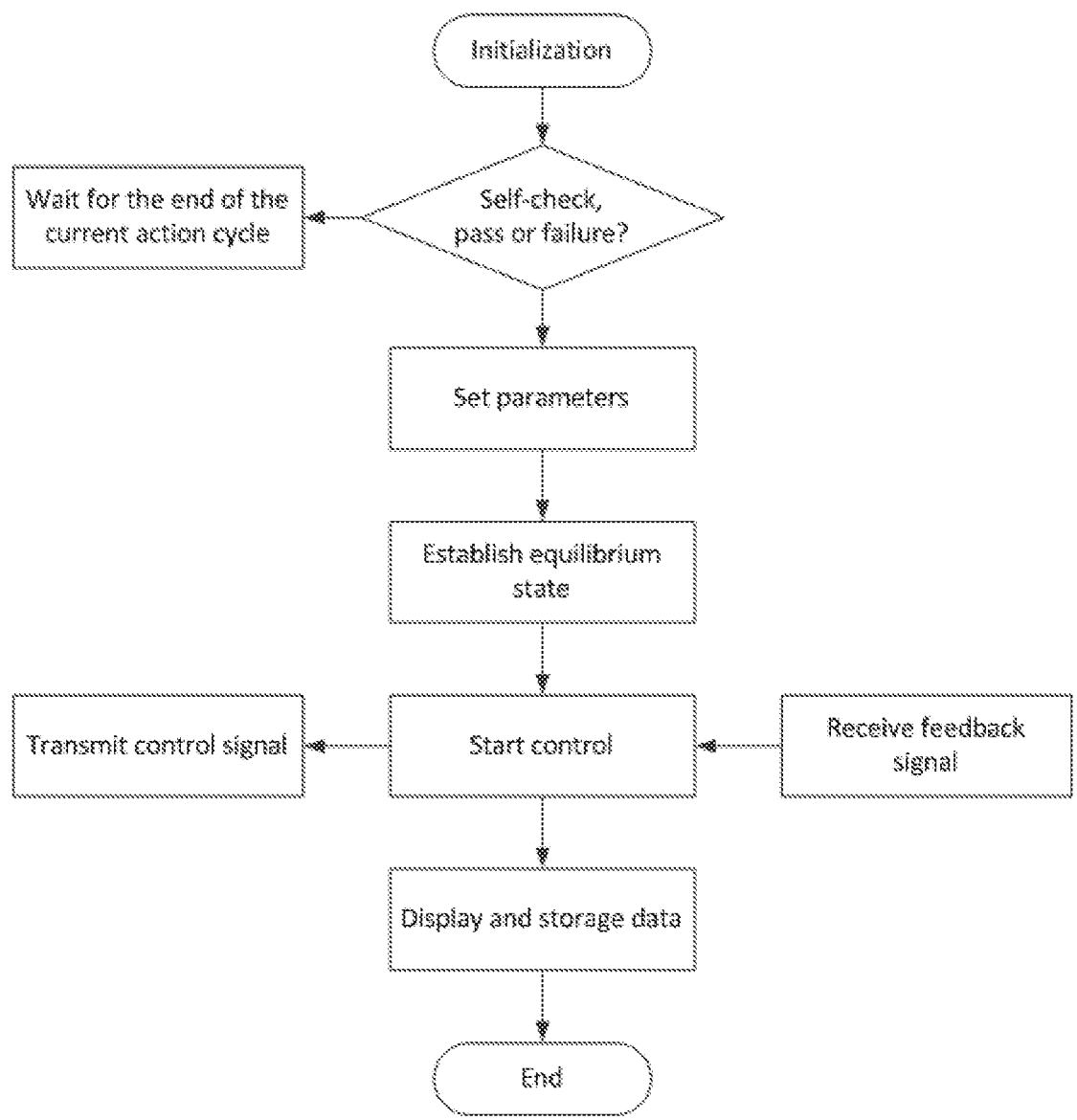
FIG. 8 is a control flow chart of the invention.

The control method of the dynamic bionic heart phantom disclosed by the invention, adopting the dynamic bionic heart phantom used for the MRI system disclosed by the invention, comprises the following steps, As shown in FIG. 8, before system control is started and after the control PC 11 (such as: computer) is turned on, the system is initialized and completes the system self-testing automatically, and is started for operation after setting motion parameters of the dynamic bionic phantom and establishing an equilibrium state. Among them, the system self-testing is used for fault diagnosis before system operation, including, valve controllability, gas path airtightness and feedback values of the proportional flow valves; and if the self-testing is failed, the system cannot run until the fault is removed. The motion parameters of the dynamic bionic phantom comprise a heart rate and a volume-time curve, wherein the heart rate setting can be selected from "heart rate setting" and "ECG setting". If the "heart rate setting" is selected, a single heart rate value may be input and a trigger mode, including, internal trigger and external trigger, may be selected; if the "ECG setting" is selected, arrhythmia models in "pathological model", including, heart rate tachycardia, premature beat, atrial fibrillation, etc., or a customized heart rate sequence can be selected. For the volume-time curve setting, data files about time-volume relationship curves of chambers may be uploaded and at least 20 time points are required. After the parameter setting is finished, the system may calculate the length of each phase period in the "heart motion period" automatically to form corresponding control timing sequences. To establish the equilibrium state is to establish an initial equilibrium state of the bionic heart phantom; based on the filling state of the P-wave atrial contraction, the proportional flow valve Ai1 and the proportional flow valve Ai2 are opened only, and after the atrium is filled to $2/3$ and the ventricle is filled to 95%, the proportional flow valve Ai1 and the proportional flow valve Ai2 are closed, at which time, the initial equilibrium state of the heart chambers is established.

Figure 7:
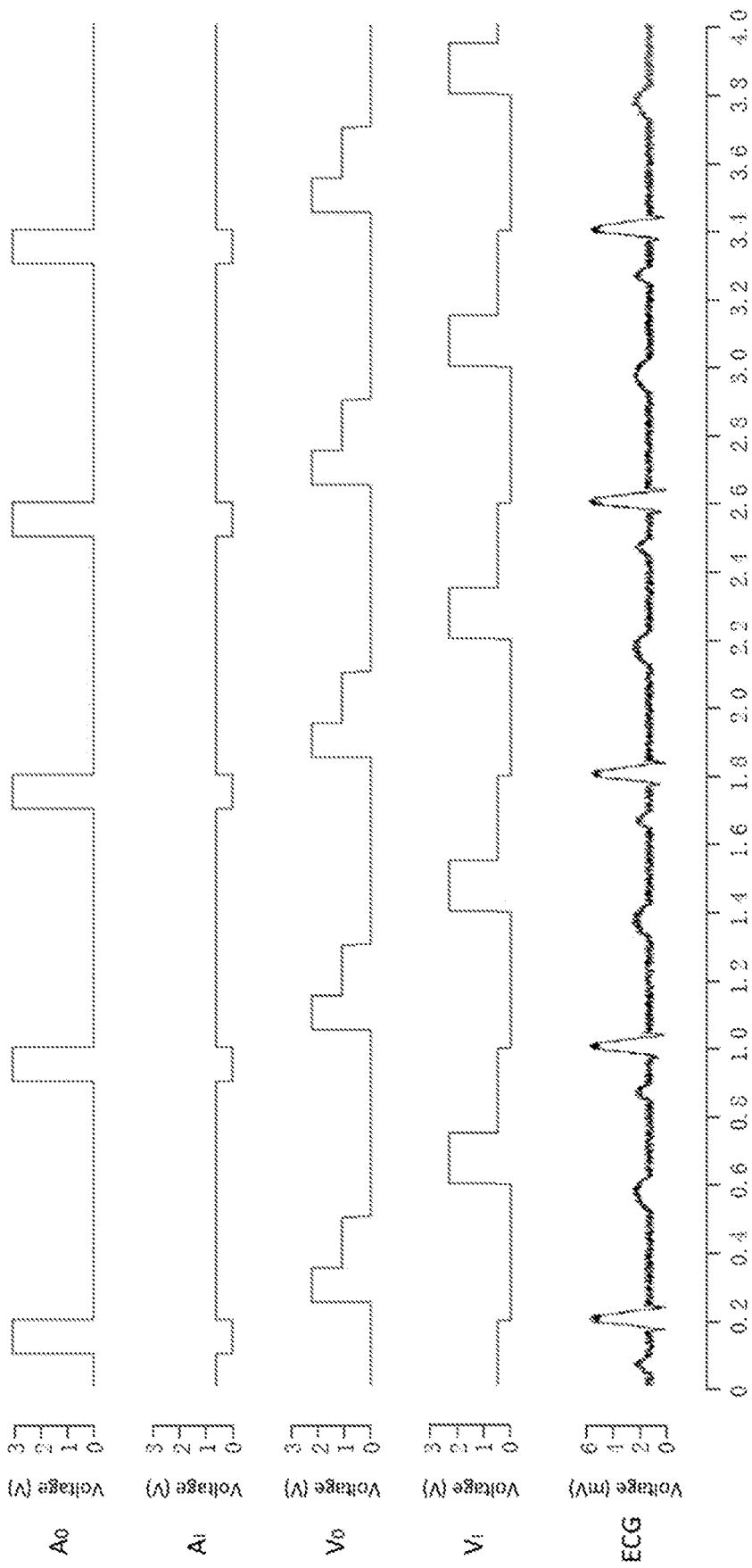
FIG. 7 is a proportional flow valve timing sequence and an ECG output waveform of software and hardware in a heart motion cycle according to the invention.

As shown in FIG. 8, the system control is started after the initial equilibrium state of the heart chambers is established, and the computer controls the multi-channel I/O interface of the measurement and control module 12 to output series pulse sequence through the USB interface (see FIG. 7), and controls opening and closing of the proportional flow valve Ai, the proportional flow valve Ai2, the proportional flow valve Vo1 and the proportional flow valve Vo2, so that the compressed gas in the gas cylinder 5 simulates blood to be filled into the bionic heart phantom, or the gas in the bionic heart phantom is discharged; each proportional flow valve 13 also feeds back the gas flow data to the control PC 11 in real time, and the control PC 11 adjusts the pulse signal based on the fed-back gas pressure or flow data; and consequently, contraction and relaxation of the bionic heart phantom for simulating the heartbeat of a human is accomplished.

A heart rate of 75 bpm (times/minute) is taken as an example below, within a 0.8 s heart motion cycle, the opening/closing states of proportional flow valves Ai1, Ai2, Vo1 and Vo2 respectively in the seven motion phase cycles, including, an atrial contraction period (0.1 s), an isovolumetric contraction period (0.05 s), a rapid ejection period (0.1 s), a slow ejection period (0.15 s), an isovolumic relaxation period (0.07 s), a rapid filling period (0.11 s) and a slow filling period (0.22 s) are as follows:

Table 2: Seven motion time phases and opening & closing state of each proportional flow valve in a heart motion cycle (75 bmp).

| Proportional flow valves | Atrial contraction period (0.1 s) | Isovolumetric contraction period (0.05 s) | Rapid ejection period (0.1 s) | Slow ejection period (0.15 s) | Isovolumic relaxation period (0.07 s) | Rapid filling period (0.11 s) | Slow filling period (0.22 s) |
| --- | --- | --- | --- | --- | --- | --- | --- |
| Ai1 | on | off | off | off | off | off | off |
| Vo1 | off | off | on | on | off | off | off |
| Ai2 | on | off | off | off | off | on | on |
| Vo2 | off | off | on | on | on | on | on |

In this embodiment, the computer outputs the ECG signals while controlling the multi-channel I/O interface of the measurement and control module 12 to output the series pulse sequence through the USB interface, and the ECG signals are transmitted to the MRI device 17 through the ECG output module and the ECG lead wire to trigger ECG gating during heart scanning of the MRI device.

In this embodiment, the ECG waveform, the proportional flow valve control timing sequences, the vacuum pump control timing sequence, the feedback flow of the flow proportional valves, and the like may also be displayed, stored, and played back in real time through a computer in the control process.

The system stops running after the testing is completed.

Figure 5:
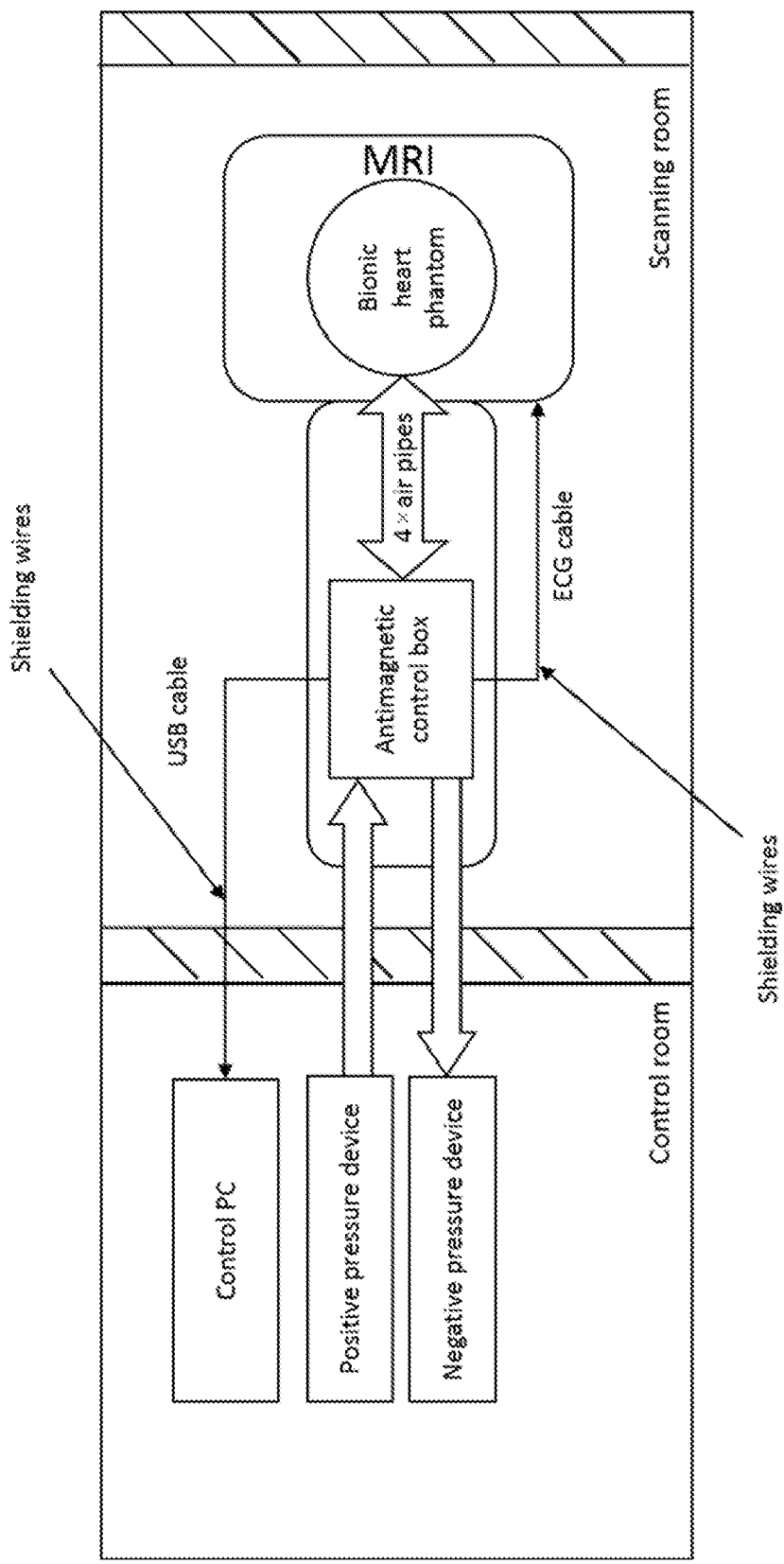
FIG. 5 is a schematic view showing the wiring of a machine room in the invention.

III. Quality Testing Method:

As shown in FIG. 5, the testing method of the imaging quality of MRI in the embodiment, adopting the dynamic bionic heart phantom used for the MRI system of the disclosure (hereinafter, the positive pressure devices in two groups are taken as an example for description), comprises the following steps:

First, placing the control PC 11, the positive pressure devices 16 and the negative pressure device in the MRI control room; putting the bionic heart phantom and the antimagnetic control device 4 on a scanning bed in the MRI scanning room; placing the bionic heart phantom in an RF coil and adjusting the bed to be in an MRI scan range; and ensuring that the antimagnetic control device 4 is located 1 m outside the edge of the main magnet of the MRI device.

Next, opening switching valves of the gas cylinders 5 of the two groups of the positive pressure devices 16, respectively and adjusting the pressure output value of the pressure reducing valves 6 within a correct range; setting control parameters in the control PC 11, starting running the system after the equilibrium state of the system is established, and, by the control PC 11, transmitting the control command to the micro processing system in real time; transmitting corresponding pulse signals to the four proportional flow valves 13 through the multi-channel I/O interface to enable the proportional flow valves 13 to be open or closed based on the received corresponding pulse signals; feeding back gas pressure or flow data to the control PC 11 in real time by the proportional flow valves 13, and adjusting the pulse signals based on the fed-back gas pressure or flow data by the control PC 11, that is, simulating the motion of the heart chambers at different heart rate cycles; generating the ECG signals while while the control PC 11 transmits the pulse signals and transmitting the signals to the MRI device 17 through the ECG output module and the ECG lead wire to trigger ECG gating during heart scanning of the MRI device, Finally, performing post-processing and 3D reconstruction by utilizing clinical application software of the MRI 17 device (such as the AW4.6 workstation of GE) to obtain relevant evaluation indexes of the bionic heart phantom, such as arrhythmia imaging success rate, morphological image quality rating and image conformity, and performing evaluation on functional conformity of the MRI device 17.

What is claimed is:

1. A dynamic bionic heart phantom used for an MRI system, comprising a bionic heart phantom, a control system, a negative pressure device and positive pressure devices, wherein the bionic heart phantom comprises a water tank, and a heart phantom arranged in the water tank; the heart phantom has four chambers, respectively including, a left atrium chamber, a right atrium chamber, a left ventricular chamber and a right ventricular chamber, among them, the left atrium chamber is connected to the left ventricular chamber through a one-way valve, and the right atrium chamber is connected to the right ventricular chamber through another one one-way valve;

the control system comprises an antimagnetic control device and a control PC; the antimagnetic control device comprises a magnetic shielding box, a measurement and control module, four proportional flow valves, a power module, an Ai1 interface, an Ai2 interface, a Vo1 interface, a Vo2 interface, an Ai1' interface, an Ai2' interface, a Vo1' interface, a J1 interface, a J2 interface and an ECG interface; the measurement and control module, the four proportional flow valves and the power module are arranged in the magnetic shielding box; the Ai1 interface, the Ai2 interface, the Vo1 interface, the Vo2 interface, the Ai1' interface, the Ai2' interface, the Vo1' interface, the J1 interface, the J2 interface and the ECG interface are arranged on the magnetic shielding box;

the measurement and control module comprises a multi-channel I/O interface, a micro processing system and an ECG output module; the micro processing system are connected to the four proportional flow valves, the ECG output module and the negative pressure device respectively through the multi-channel I/O interface to transmit corresponding control signals to the four proportional flow valves and a vacuum pump, transmit ECG analog signals to the ECG output module at the same time and collect feedback signals of the four proportional flow valves in real time;

the four proportional flow valves include a proportional flow valve Ai1, a proportional flow valve Ai2, a proportional flow valve Vo1, and a proportional flow valve Vo2; a gas outlet end of the proportional flow valve Ai1 is connected with the right atrium chamber of the heart phantom through the Ai1 interface and an air pipe while a gas inlet end thereof is connected to the positive pressure devices through the Ai1' interface and the air pipe; a gas outlet end of the proportional flow valve Ai2 is connected to the left atrium chamber of the heart phantom through the Ai2 interface and the air pipe while a gas inlet end thereof is connected to the positive pressure devices through the Ai2' interface and the air pipe; a gas outlet end of the proportional flow valve Vo1 is connected to the right ventricular chamber of the heart phantom through the Vo1 interface and the air pipe while a gas inlet end thereof is connected to the negative pressure device through the Vo1' interface and the air pipe; a gas outlet end of the proportional flow valve Vo2 is connected to the left ventricular chamber of the heart phantom through the Vo2 interface and the air pipe while a gas inlet end thereof is connected to the negative pressure device through the Vo2' interface and the air pipe; the four proportional flow valves are also connected to the measurement and control module respectively to receive control signals and transmit feedback signals; and the power module is connected to the measurement and control module and the four proportional flow valves respectively to provide working power to the measurement and control module and the four proportional flow valves.

2. The dynamic bionic heart phantom used for the MRI system according to claim 1, wherein the ECG output module comprises a high precision operational amplifier differential circuit, a resistance network circuit and an LA electrode interface, an RA electrode interface, and an LL electrode interface and an RL electrode interface; the resistance network circuit is connected to the high precision operational amplifier differential circuit and is also connected to the LA electrode interface, the RA electrode interface, the LL electrode interface, and the RL electrode interface to convert the analog signals transmitted by the micro processing system to ECG signals for simulating limb leads; and the LA electrode interface, the RA electrode interface, the LL electrode interface and the RL electrode interface are connected to the MRI device via an ECG lead wire through an ECG interface of the antimagnetic control device.

3. The dynamic bionic heart phantom used for MRI system according to claim 1, wherein the magnetic shielding box comprises a box, a top cover, a handle and connectors, all of which are made of aluminum plates; and ten extension tubes with waveguide holes, respectively used for installation of eight air pipes, one shielding wire, one USB cable with the shielding wire and the ECG lead wire, are arranged on both sides of the box.

4. The dynamic bionic heart phantom used for the MRI system according to claim 3, wherein two groups of the positive pressure devices are provided, each of which, comprises a gas cylinder and a pressure reducing valve; the gas cylinder, filled with gas, is connected with the pressure reducing valve; the gas inlet end of the proportional flow valve Ai1 is connected to one of the positive pressure devices having a pressure output value of 0.5 MPa at the Ai1 interface through the Ai1' interface and the air pipe; and the gas inlet end of the proportional flow valve Ai2 is connected to another one of the positive pressure devices with the pressure output value of 1.5 Mpa at the Ai2 interface through the Ai2' interface and the air pipe.

5. The dynamic bionic heart phantom used for the MRI system according to claim 3, wherein the negative pressure device comprises a vacuum pump and a negative pressure container; the vacuum pump is connected to the antimagnetic control device through the shielding wire to receive control signals and is also connected to the negative pressure container through the air pipe; and the negative pressure container is connected to the Vo1' interface and the Vo1' interfaces of the antimagnetic control device through the air pipes to receive gases.

6. The dynamic bionic heart phantom used for the MRI system according to claim 5, wherein the multi-channel I/O interface is connected to the analog input interfaces of the four proportional flow valves respectively through four analog output interfaces, and the analog input interfaces of the proportional flow valves—are used for receiving control pulse signals;

the multi-channel I/O interface is connected to the analog output interfaces of the four proportional flow valves respectively through eight analog input interfaces, and the analog output interfaces of the proportional flow valves are used for feedback of gas pressure or flow data;

the multi-channel I/O interface is connected to the ECG output module through an analog output interface to output ECG analog signals;

the multi-channel I/O interface is connected to the vacuum pump via the J2 interface of the antimagnetic control device and the shielding wire through one analog output interface to output control driving signals; and the multi-channel I/O interface is connected to the control PC via the J1 interface of the antimagnetic control device through the USB cable with the shielding wire.

7. A control method of the dynamic bionic heart phantom, using the dynamic bionic heart phantom used for the MRI system according to claim 1, wherein the control method comprises following steps:

the control PC transmits corresponding pulse signals to the four proportional flow valves respectively through the multi-channel I/O interface, and the proportional flow valves are open or closed based on the received corresponding pulse signals; each proportional flow valve feeds back gas pressure or flow data to the control PC in real time, and the control PC adjusts the pulse signals based on the fed-back gas pressure or flow data, that is, simulates a motion of heart chambers at different heart rate cycles; the control PC also generates ECG signals while transmitting the pulse signals, and transmits the signals to the MRI device through the ECG output module and an ECG lead wire to trigger ECG gating during heart scanning of the MRI device.

8. A testing method of the imaging quality of the MRI device, using the dynamic bionic heart phantom used for the MRI system according to claim 1, wherein the testing method comprises following steps:

first, placing the control PC, the positive pressure devices and the negative pressure device in a MRI control room; putting the bionic heart phantom and the antimagnetic control device on a scanning bed in the MRI scanning room; placing the bionic heart phantom in an RF coil and adjusting the scanning bed to be in an MRI scan range; and ensuring that the antimagnetic control device is located 1 m outside an edge of a main magnet of the MRI device;

next, opening the positive pressure devices respectively; setting control parameters in the control PC, starting running a system after an equilibrium state thereof is built and, by the control PC, transmitting a control command to the micro processing system in real time; transmitting corresponding pulse signals to the four proportional flow valves through the multi-channel I/O interface to enable the proportional flow valves to be open or closed based on the received corresponding pulse signals; feeding back gas pressure or flow data to the control PC in real time by each of the proportional flow valves and adjusting the pulse signals based on the fed-back gas pressure or flow data by the control PC, that is, simulating a motion of the heart chambers at different heart rate cycles; generating ECG signals while the control PC transmits the pulse signals, and transmitting the signals to the MRI device through the ECG output module and an ECG lead wire to trigger ECG gating during heart scanning of the MRI device; and finally, performing post-processing and 3D reconstruction by utilizing clinical application software of the MRI device to obtain relevant evaluation indexes of the bionic heart phantom, and performing evaluation on functional conformity of the MRI device.

* * * * *